US006180111B1

(12) United States Patent
Stein et al.

(10) Patent No.: US 6,180,111 B1
(45) Date of Patent: Jan. 30, 2001

(54) VACCINE DELIVERY SYSTEM

(75) Inventors: Daniel C. Stein, Silver Spring, MD (US); Charles K. Stover, Mercer Island, WA (US)

(73) Assignee: University of Maryland, College Park, MD (US)

( * ) Notice: Under 35 U.S.C. 154(b), the term of this patent shall be extended for 0 days.

(21) Appl. No.: 09/081,576

(22) Filed: May 19, 1998

Related U.S. Application Data

(63) Continuation-in-part of application No. 08/936,522, filed on Sep. 23, 1997, now abandoned, which is a continuation of application No. 08/443,514, filed on May 18, 1995, now abandoned.

(51) Int. Cl.$^7$ .................................................. A61K 39/095
(52) U.S. Cl. ................................... 424/249.1; 424/200.1; 424/234.1; 424/250.1; 424/184.1; 424/203.1; 424/269.1; 435/243; 435/252.3; 435/9.1; 435/69.3; 435/69.5; 435/71.1; 435/71.2; 435/172.1; 530/350; 530/351; 530/812; 536/1.11
(58) Field of Search .............................. 424/250.1, 249.1, 424/234.1, 269.1, 200.1, 203.1, 184.1; 435/69.1, 69.3, 71.1, 71.2, 172.1, 243, 252.3, 69.5; 530/350, 812, 351; 536/1.11

(56) References Cited

PUBLICATIONS

Ferron. Dissertation Abstracts International. vol. 57/04–C, p. 1160. 1995.*
Wetzler et al. J. Infec. Dis. Sep. 1992. 166(3): 551–5 * Abstract only, Sep. 1992.*
S.B. Snapper et al., "Lysogeny and Transformation in Mycobacteria: Stable Expression of Foreign Genes", Proc. Natl. Acad. Sci. USA, vol. 85, pp. 6897–6991, 1988.
W.R. Jacobs et al., "Development of BCG as a Recombinant Vaccine Vehicle", Cur. Top. Microbio. And Immuno., vol. 155, pp. 152–160, 1990.
S.M.C. Newton et al., "Immune Response to Cholera Toxin Epitope Inserted in *Salmonella Flagellin*", Science, vol. 244, pp. 70–72, 1989.
A. Charbit et al., "Probing the Topology of a Bacterial Membrane Protein by Genetic Insertion of a Foreign Epitope; Expression at the Cell Surface"; Embo J., vol. 5, pp. 3029–3037, 1986.

A. Reitermann et al., "Lipopeptide Derivatives of Bacterial Liproprotein Constitute Potent Immune Adjuvants Combined With or Covalently Coupled to Antigen or Hapten", Biol. Chem Hoppe–Seyler, vol. 370, pp. 343–352, 1989.
American Academy of Pediatrics, Committee on Infections Diseases, "Haemophilus Influenzae Type B Conjugate Vaccines: Recommendations For Immunization of Infants and Children 2 Months of Age and Older: Update", Pediatrics, vol. 88, No. 1, pp. 169–172, 1991.
C. K. Stover et al., "New Use of BCG for Recombinant Vaccines", Nature, vol. 351, pp. 456–460, 1991.
J. Fu et al., "Recent Advances in the Large Scale Fermentation of Neisseria *Gonorrhoeae* Group B for the Production of an Outer Membrane Protein Complex", Bio/Technology, vol. 13, pp. 170–174, 1995.
R. N. Husson et al., "Gene Replacement and Expression of Foreign DNA in Mycobacteria", J. Bacter, vol. 172, pp. 519–524, 1990.
David W. Dorward et al., "Export and Intercellular Transfer of DNA via Membrane Blebs of *Neisseria Gonorrhoeae*", Journal of Bacteriology, vol. 171, No. 5, pp. 2499–2505, 1989.
D. C. Stein et al., "Role of Restriction and Modification on Genetic Exchange in *Neisseria Gonorrhoeae*", Gonococci and Meningucocci, 5$^{th}$ Annual *Neisseria* Conference pp. 323–327, 1988.
David W. Dorward et al., "DNA–Binding Proteins in Cells and Membrane Blebs of *Neisseria Gonorrhoeae*", Journal of Bacteriology, vol. 171, No. 8, pp. 4196–4201, 1989.
Emanual F. Petricoin, III et al., "Molecular Analysis of Lipooligosaccharide Biosynthesis in *Neisseria Gonorrhoeae*", Infection and Immunity, vol. 57, No. 9, pp. 2847–2852, 1989.

* cited by examiner

*Primary Examiner*—Jennifer Graser
(74) *Attorney, Agent, or Firm*—Long Aldridge & Norman

(57) ABSTRACT

The invention relates to a hyperblebbing strain of *Neisseria gonorrhoeae* which produces large amounts of blebs useful for production of blebosomes containing antigens for use as a vaccine delivery vehicle or as a diagnostic reagent. The invention also relates to a method for producing high levels of a desired protein in purified form using the hyperblebbing strain of *N. gonorrhoeae*, and to a vaccine delivery systems containing the blebosomes expressing the desired antigen.

19 Claims, 9 Drawing Sheets

SEQUENCE LISTING

```
<160> NUMBER OF SEQ ID NOS:  13

<210> SEQ ID NO 1
<211> LENGTH: 46
<212> TYPE: DNA
<213> ORGANISM: Neisseria gonorrhoeae

<400> SEQUENCE: 1
gaattcgagc tcggtacccg gggatcagaa ttcagacggc tgatcc                  46

<210> SEQ ID NO 2
<211> LENGTH: 32
<212> TYPE: DNA
<213> ORGANISM: Neisseria gonorrhoeae

<400> SEQUENCE: 2
tctagagtcg acctgcaggc atgcaagctt gg                                 32

<210> SEQ ID NO 3
<211> LENGTH: 27
<212> TYPE: DNA
<213> ORGANISM: Neisseria gonorrhoeae

<400> SEQUENCE: 3
ccctgaattc aaatcatact gaattat                                       27

<210> SEQ ID NO 4
<211> LENGTH: 19
<212> TYPE: DNA
<213> ORGANISM: Neisseria gonorrhoeae

<400> SEQUENCE: 4
ccgatcagtt caaaactgc                                                19

<210> SEQ ID NO 5
<211> LENGTH: 17
<212> TYPE: DNA
<213> ORGANISM: Neisseria gonorrhoeae

<400> SEQUENCE: 5
ggctgcatgc ggcggag                                                  17

<210> SEQ ID NO 6
<211> LENGTH: 19
<212> TYPE: DNA
<213> ORGANISM: Neisseria gonorrhoeae

<400> SEQUENCE: 6
```

-continued

```
ccgccgcatg cagccaaag                                              19

<210> SEQ ID NO 7
<211> LENGTH: 30
<212> TYPE: DNA
<213> ORGANISM: Neisseria gonorrhoeae

<400> SEQUENCE: 7
attccagtcg acaagcaaaa tgttagcagc                                  30

<210> SEQ ID NO 8
<211> LENGTH: 36
<212> TYPE: DNA
<213> ORGANISM: Neisseria gonorrhoeae

<400> SEQUENCE: 8
attccagcat gcttatttta aagcgttttt aatttc                           36

<210> SEQ ID NO 9
<211> LENGTH: 35
<212> TYPE: DNA
<213> ORGANISM: Neisseria gonorrhoeae

<400> SEQUENCE: 9
gaattcagga gaaaatctaa tgaacaaatt tgtta                            35

<210> SEQ ID NO 10
<211> LENGTH: 36
<212> TYPE: DNA
<213> ORGANISM: Neisseria gonorrhoeae

<400> SEQUENCE: 10
gaattcagga gaaaatctaa tgaacaaatt tgttaa                           36

<210> SEQ ID NO 11
<211> LENGTH: 19
<212> TYPE: DNA
<213> ORGANISM: Neisseria gonorrhoeae

<400> SEQUENCE: 11
aatcgcatga ttccttaag                                              19

<210> SEQ ID NO 12
<211> LENGTH: 41
<212> TYPE: DNA
<213> ORGANISM: Neisseria gonorrhoeae

<400> SEQUENCE: 12
gcggaattca gaggtaaatt tagatgaata agaaaaaaat g                     41

<210> SEQ ID NO 13
<211> LENGTH: 21
<212> TYPE: DNA
<213> ORGANISM: Neisseria gonorrhoeae

<400> SEQUENCE: 13
tgaggtcagc tgattcttaa g                                           21
```

VACCINE DELIVERY SYSTEM

CROSS-REFERENCE TO RELATED APPLICATIONS

This application is a continuation-in-part application of U.S. Ser. No. 08/936,522 filed on Sep. 23, 1997 now abandoned which is a continuation of U.S. Ser. No. 08/443,514 filed on May 18, 1995, now abandoned.

GOVERNMENT SUPPORT

This work was supported by grant AI 24452 from the National Institutes of Health. The government may have certain rights in this application.

BACKGROUND OF THE INVENTION

1. Field of the Invention

The present invention provides compositions comprising blebosomes which express an immunogenic polypeptide specific for a disease, methods of manufacturing the same, methods for detecting antibodies specific for said immunogenic polypeptides and methods for immunizing an animal using said blebosomes.

2. Discussion of the Background

Immunization is a principal feature for improving the health of infants and young children. Despite the availability of a variety of successful vaccines against most of the common childhood illnesses, infectious diseases remain a leading cause of death in children. Significant problems inherent in existing vaccines include the need for repeated immunizations, and the ineffectiveness of the current vaccine delivery systems for a broad spectrum of diseases.

The number of successful approaches to vaccine development is almost as broad as the number of infectious agents. As technology has developed, it has become possible to define at the molecular level the nature of the protective immunogen. In recent years, acellular vaccines have become the method of choice for vaccine development because they can be administered with subunits from a variety of pathogens (i.e. multicomponent vaccines) and they have the potential for reduced numbers of adverse reactions. Subunit vaccines are composed of defined purified protective antigens from pathogenic microorganisms.

Perhaps the best example of success with subunit vaccines is the current vaccine that prevents diseases caused by *H. influenzae*. A conjugate vaccine composed of *H. influenzae* polyribosyl ribitol phosphate (PRP) capsular polysaccharide conjugated to an outer membrane protein complex (OMPC) from *N. meningitidis* has proven to be safe and effective in generating protective immune responses in infants as young as 2 months of age. Covalent coupling of PRP to OMPC results in a conjugate that effectively mediates carrier priming and additionally provides an insoluble particulate antigen containing lipooligo-saccharides (LOS) which have adjuvant activity. This vaccine is widely accepted as safe and effective in reducing the incidence of morbidity and mortality associated with diseases caused by *H. influenzae* (Stover, C. K. et al., *Nature* 351:456–460, 1991; Husson, R. N. et al., *J. Bacteriol.* 172: 519–524, 1990; Jacobs, W. R. et al., *Curr. Top. Microbiol. Immunol.* 155:153–160, 1990; Jacobs, W. R. et al., *Nature* 327: 532–535, 1987. All documents cited herein are hereby incorporated by reference).

Although there have been a few stunning successes, a small number of subunit vaccines are currently in use. Perhaps the most daunting reason impeding the use of subunit vaccines is the problem of antigen delivery. For optimal antigen delivery, the antigen needs to be delivered to the antigen presenting cells in its biological context, or the antigen needs to be readily recognized and taken up by phagocytes. Most antigens possess three dimensional structures that are important for parasite-host cell interactions and many of these structures are lost during antigen purification.

One approach taken to circumvent most of the problems associated with subunit vaccine production is the development of live recombinant vaccine vehicles, based on attenuated viruses and bacteria that have been genetically engineered to express protective antigens in vivo (i.e. recombinant forms of vaccinia virus, adenovirus, Salmonella and mycobacterium tuberculosis typhus bonivur var. Bacille-Calmette-Guerin or BCG) (Snapper, S. B. et al., *Proc. Natl. Acad. Sci USA* 85:6987–6991, 1988; Jackett, P. S. et al., *J. Clin. Micro.* 26:2313–2318, 1988; Lamb, J. R. et al., *Rev. Infect. Dis.* 11:S443–S447, 1989; Shinnick, T. M. et al., *Infect. Immun.* 56:446–451, 1988).

Live vaccines present advantages in that the antigen is expressed in the context of an innately immunogenic form; the live delivery system replicates and persists in the host, restimulating the host immune system and obviating the need for multiple doses; live vector systems eliminate the need to purify the antigen, and are less expensive to produce; and live vectors can be designed to deliver multiple antigens, reducing the number of times an individual must be vaccinated.

Investigators developing *Escherichia coli* and Salmonella as live vaccine vehicles have developed export vectors utilizing flagella, fimbriae or major outer membrane proteins (OmpA and LamB) as carriers to export protective epitopes to the surface of the bacterial vaccine vehicle (Stover, C. K. et al., *Infect. Immun.* 58: 1360–1475, 1990; Thole, J. E. R. et al., *Infect. Immun.* 55:1466–1475, 1988). However, the approach of grafting epitopes into these surfaces is limited, as only small epitopes may be inserted, and the epitopes are presented in a context of a foreign protein that may limit its ability to assume its native conformation.

In order to develop vaccines against pathogens that have been recalcitrant to vaccine development, and/or to overcome the failings of commercially available vaccines due to underutilization, new methods of antigen presentation must be developed which will allow for fewer immunizations, and/or fewer side effects to the vaccine. A new vaccine delivery system is described in this application which is based on *Neisseria gonorrhoeae* as a host, a bacterium that naturally turns over its outer membrane into easily isolated immunogenic blebs.

*N. gonorrhoeae* is a human pathogen of mucosal surfaces. *N. gonorrhoeae* is a Gram-negative bacteria with an undulating outer membrane which appears as a bilayered structure (Reviewed In: *The Gonococcus*, P. B. Roberts (Ed.). Wiley, New York). The chromosome of the gonococcus contains approximately $2.1 \times 10^6$ nucleotide pairs. During log phase, the gonococcus forms cell wall blebs which are produced by budding of the outer membrane (Schorr, J. B. et al., *Cold Spring Harbor Laboratory Press Vaccines* 91:387–392, 1991). These blebs are spherical and are surrounded by a bilayer membrane-like structure. Blebs derived from Neisseria have a liposomal three-dimensional structure and provide immune stimulation (adjuvant activities) to antigens covalently coupled to them (Brandt, M. E. et al., *Infect. Immun.* 58:983–991, 1989). Protein profiles from gonococcal blebs closely resemble those proteins seen in the outer membrane of the gonococcus (Melchers, F. et al., *J. Exp. Med.* 142:473–482, 1975). Gonococcal blebs contain on their surface proteins I (Pistor, S. and G. Hobom, Wochenschr. 66:110, 1988), II (Bakker, D. et al., *Microb. Path.* 8:343–352, 1990), and H8 (Charbit, A. et al., EMBO 5(11):3029–3037, 1986). In addition, they contain gonococcal lipooligosaccharide (LOS).

Much work has been done on characterizing the cell surface antigens of the gonococcus, and many of the genes encoding the protein antigens have been cloned and their DNA sequences determined (Vodkin, M.H. and Williams, J. C., *J. Bact.* 170:1227–1234, 1988; Young, D. L. et al., *Infect. Immun.* 54(l):177–183, 1986; Young, D. R. et al., *Proc. Natl. Acad. Sci.* U.S.A 85:4267–4270, 1998; Newton, S. M. et al., Science 244:70–244, 1989). Studies on biosynthesis and the genetics underlying the biosynthesis of each of the LOS components are far enough along to allow for the successful construction of strains with a defined LOS structure and a stable cell surface. Neisseria mutants that are deficient for LOS and other cell surface proteins have been well described and can be easily produced. Furthermore, gonococcal blebs are easy to isolate and vectors for the genetic manipulations of Neisseria already exist.

Blebosomes are advantageous over liposomes as carriers of antigens. Liposomes are artificially made and proteins of interest are either entrapped in them or chemically conjugated to their surface. The blebosomes of the present invention require no special treatment, and proteins are folded naturally by native enzymes and can be engineered to be expressed inside or outside the bleb.

The present invention provides a vaccine delivery system comprising engineered *N. gonorrhoeae* wherein, said bacteria expresses and directs any heterologous target antigen to its outer membrane. The outer membrane with the antigenic protein is naturally sloughed off in gonococcal blebs during cell growth. The resulting target antigen-membrane bleb complex or blebosome is easy to isolate and would represent a non-living but immunogenic cell-like particle which can be used to elicit a protective immune response.

Free blebbing, or hyperblebbing strains allow for the necessary production of large amounts of blebosomes for use in a vaccine. In order to commercially produce a vaccine based on gonococcal blebs, it must be possible to produce large quantities of blebosomes. Although all gonococcal strains produce blebs, the yield tends to be low, and prohibitive for use as a vaccine delivery system. A strain that hyperblebs gives the required high yield of blebs for economic production of a vaccine. Such a hyperblebbing strain has not yet been described in the literature. Therefore, there is a need for a strain of *N. gonorrhoeae* which is able to hyperbleb in order to economically produce quantities of blebosomes containing the target antigens in amounts sufficient for use as a vaccine delivery system.

SUMMARY OF THE INVENTION

The present invention is directed to a mutant of *N. gonorrhoeae* strain WR302 that is defective in an unknown growth parameter. This defect causes the gonococcus to grow abnormally and slough off its outer membrane at a very high frequency or hyperbleb. This strain produces many more outer membrane vesicles (blebs) than other strains and the blebs are readily visualized by electron microscopy.

The present invention is also directed to the production of other *N. gonorrhoeae* strains with the hyperblebbing phenotype by using a non-selective spot transformation technique. This technique allows for easy identification of transformants of *N. gonorrhoeae* in the absence of selective pressure. The technique comprises the steps of mixing a limiting number of cells with an excess amount of DNA, spotting the mix onto the surface of an agar plate, incubating the mix, and re-streaking and selecting the transformed cells. The hyperblebbing strains are altered in their expression of lipooligosaccharide (LOS). The transformants can be identified phenotypically based on their acquisition of new monoclonal antibody reactivity and the diffusion of blebs away from the colony.

By using the spot-transformation technique described above on strains of *N. gonorrhoeae* with different mutations and/or already possessing genes for different antigens, hyperblebbing strains of *N. gonorrhoeae* expressing antigens for different diseases can be produced. Blebosomes collected from these hyperblebbing strains can be used to produce a vaccine for immunization against these diseases. Vaccines produced in this way have an advantage over whole cell vaccines because the antigens are present in the absence of other cellular components. In addition, the antigens are assembled in a natural biological membrane allowing the antigen to form a native conformation, more closely mimicking what is encountered in the natural organism.

These blebosomes can be used in diagnostic assays wherein the presence of antibodies against disease can be detected in samples from a patient suspected of having the disease.

Blebosomes can also be used as a delivery system for other biologically made molecules, such as chemotherapeutic agents for use in chemotherapy, or immune enhancers/suppressors or antibiotics.

Further, the blebosomes can be used to expedite the purification of membrane proteins from the gonococcus (either natural or engineered). Blebosomes are significantly enriched for outer membrane proteins of the gonococcus since most of the cells cytoplasmic components are absent. Isolation of blebosomes then represents a significant purification of those gonococcal membrane proteins. Similarly, blebosomes can be enriched for proteins which have been engineered to be expressed in the blebosome, for example a receptor protein, and would offer a significant improvement in aiding in the production and purification of such proteins.

Therefore, it is an object of the present invention to provide a hyperblebbing strain of *Neisseria gonorrhoeae* which produces large amounts of blebs useful for the production of blebosomes containing specific antigens for use as a vaccine delivery vehicle or as a diagnostic agent.

It is another object of the present invention to provide a method for the production of hyperblebbing strains of *N. gonorrhoeae.*

It is another object of the present invention to provide a method for the production of large amounts of a desired protein in purified form, said method comprising introducing the desired gene into a hyperblebbing strain of *N. gonorrhoeae* such that the protein is expressed in blebosomes, and isolating said blebosomes.

It is yet another object of the present invention to provide a vaccine delivery system comprising the blebosomes expressing an antigen specific for said disease which would provide immunity against said disease.

DRAWINGS

These and other features, aspects and advantages of the present invention will become better understood with regard to the following description, appended claims, and accompanying drawing where:

FIG. 1 shows an immunoblot of the hyperblebbing *N. gonorrhoeae.*

FIG. 2 shows partial restriction maps and depiction of detections constructed for the S. NgoI, II, IV, V, and VII R/M system clones. Arrows show the predicted methyltransferase (M) and restriction endonuclease (R) open reading frames. The black boxes represent the deleted regions on each clone. Restriction site abbreviations are B, BglI; C, ClaI; D, DraI; E, EcoRI; H, HindIII; Hp, HpaI; N, NcoIII; P, PstI; R, RsaI; S, SalI; Sm, SmaI; Sp, SphI; Ss, SspI; St, StyI; Su, Sau3AI; U, gonococcal uptake sequence; and X, XhoI.

FIG. 3 illustrates the spot transformation technique.

FIG. 4 represents an autoradiogram of Southern blots confirming the incorporation of R/M deletions into the chromosome. The first lane of each set is DNA from FA 19 and the second lane form JUG029. Set 1, NgoI deletion (probed with PstI-XhoI fragment of pLJPC30); Set 2, NgoII deletion (probed with pLV155); Set 3, NgoIV deletion (probed with pCBB49.0); Set 4, NgoV deletion (probed with pJM5); Set 5, NgoVII deletion (probed with pF,63). DNAs were digested with Set 1, DraI; Set 2, Sau3AI; Set 3, SspI; Set 4, RsaI; Set 5, EcoRI+HindIII.

FIG. 5 shows an assay for the lack of S. NgoI, II, IV, V, and VII MTase activity in strain JUG029. The first lane of each set is DNA isolated from FA 19 and the second lane from JUG029. Each set is digested with its isoschizomer (or an enzyme with an overlapping recognition sequence). Set 1, HaeII (NgoI); Set 2, HaeIll (NgoII); Set 3, NgoMI (NgoIV); Set 4, BamHI (NgoV); Set 5;, Fnu4HI (NgoVII). Lane M is lambda HindIII marker.

FIG. 6 shows PCR primers used to amplify the p6 and pspA genes. FIG. 6A shows the primers (SEQ ID NOS: 9–11) used to amplify the p6 gene. FIG. 6B shows the primers used to amplify the pspA gene.

FIG. 7 shows plasmid maps of pLEE20 containing the p6 and pspA inserts. FIG. 7A shows pLEE20-p6, which is approximately 6.6 kb. The p6 gene has its own lipoprotein sequence and is translated from its own ATG. Erm= Erythromycin®. FIG. 7B shows pLEE20-pspA. pspA is also translated from its own ATG.

DESCRIPTION

Hyperblebbing Strains

Figure 1:
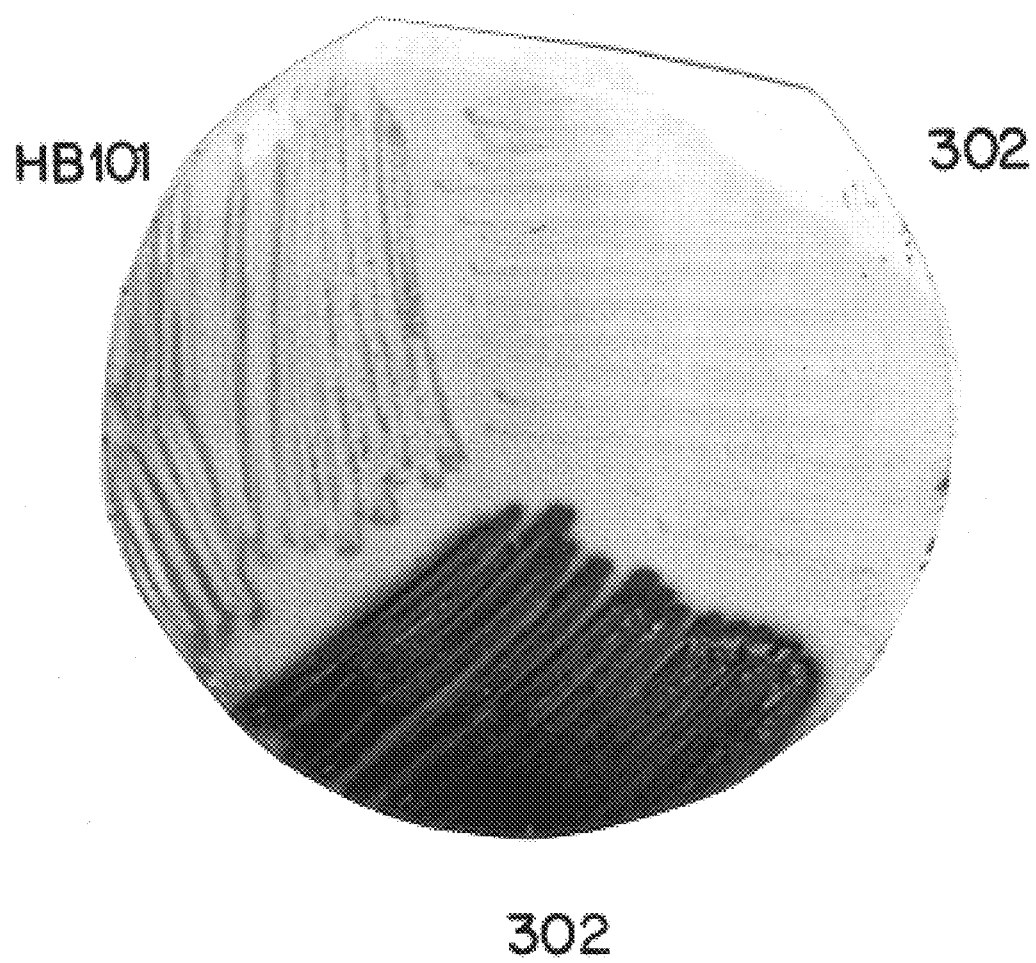
Figure 2:
Figure 3:
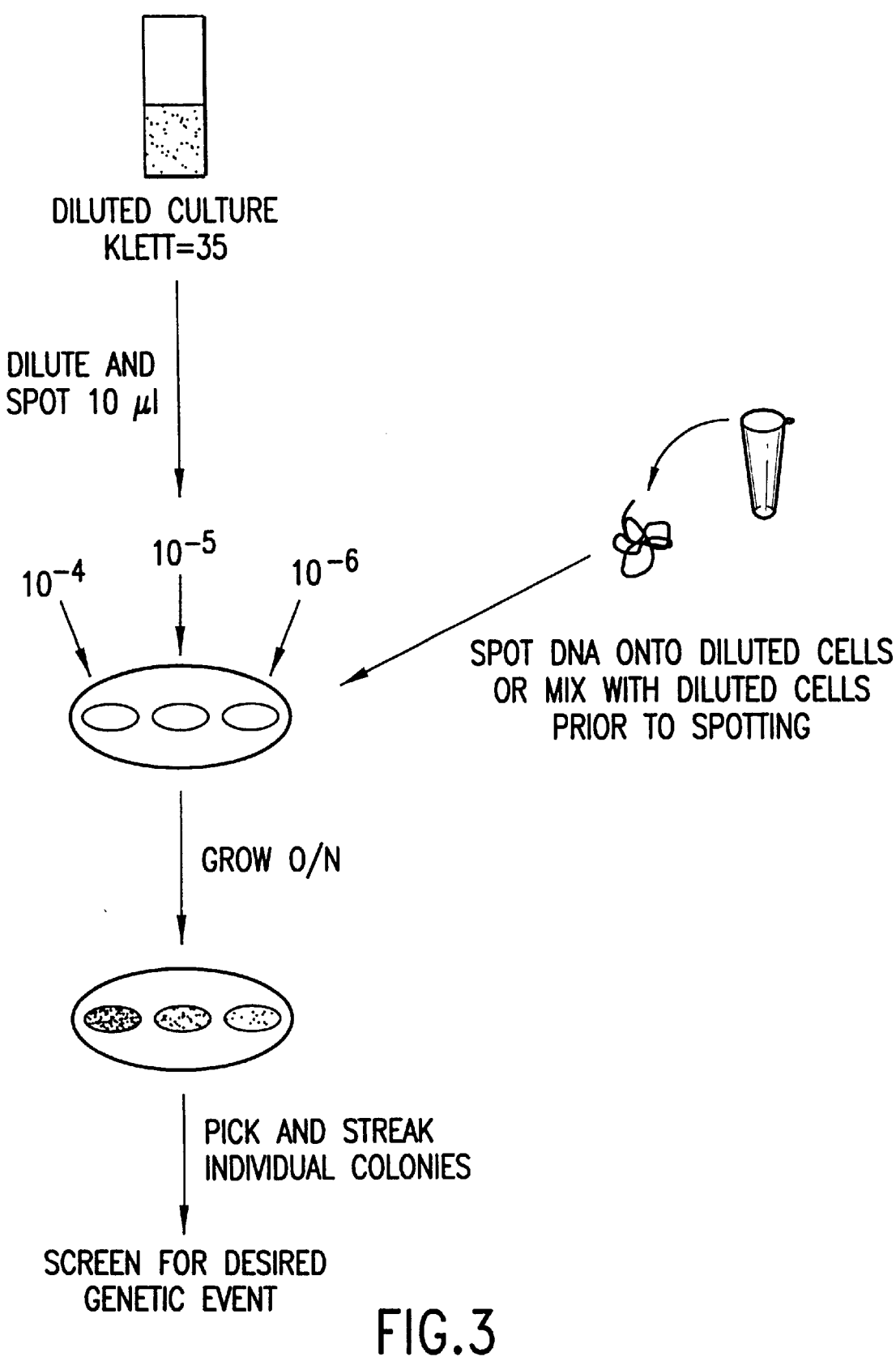
Figure 4:
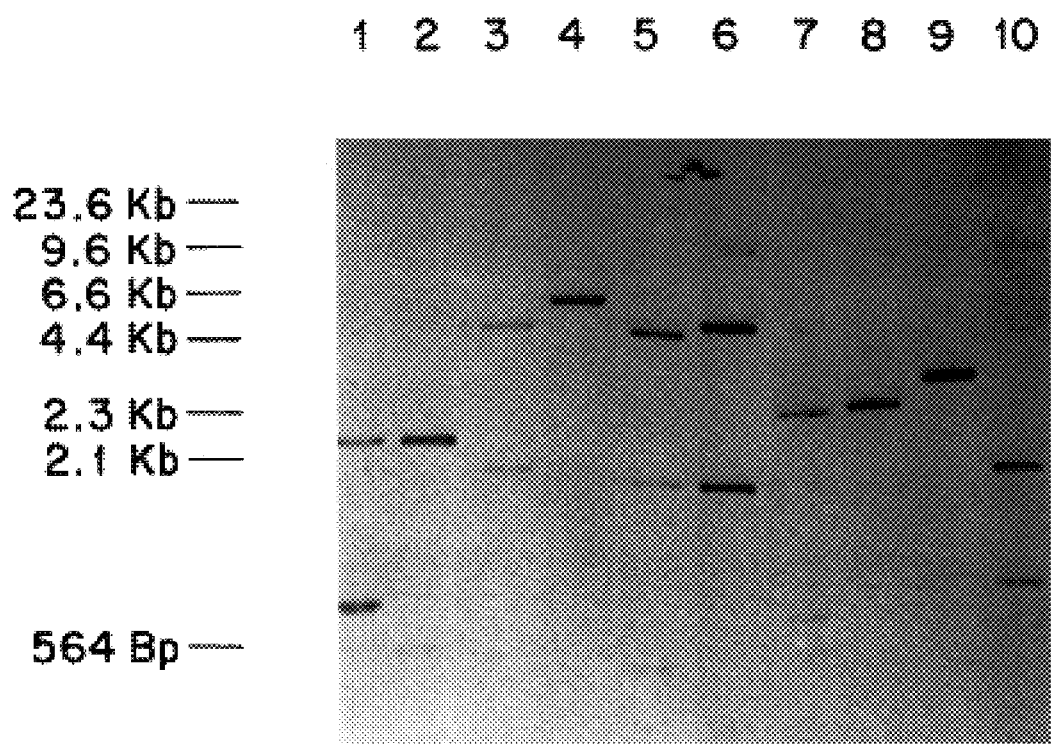
Figure 5:
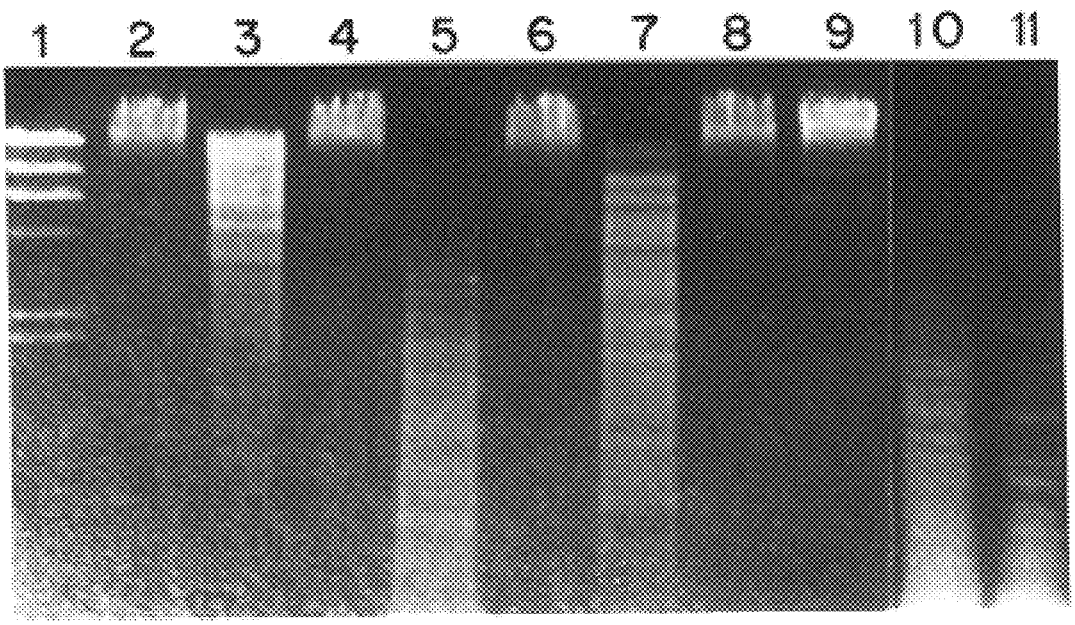

The present invention relates to hyperblebbing *N. gonorrhoeae*. "Hyperblebbing", as used herein, means that the mutant strain blebs more than the parent strain from which it was obtained. In general, hyperblebbing mutants bleb greater than 10% more than their parent strains, preferably greater than 20%, more preferably greater than 30%.

The hyperblebbing *N. gonorrhoeae* can be prepared and selected as described in the Examples that follow. For example, two approaches could be used to construct a hyperblebbing strain. The most precise approach would be to identify the genetic basis of this mutation, and clone the gene.

The second approach is the non-selective spot transformation method which was described in the Examples that follow. Briefly, chromosomal DNA isolated from the hyperblebbing strain are used to transform a wild type strain. The hyperblebbing phenotype is easily identified because strains that hyperbleb react with LOS-specific monoclonal antibodies 2-1-L8 and 1B2 on colony blots, for example. Monoclonal antibody 2-1-L8 can be obtained from Dr. Wendel Zollinger, Walter Reed Army Institute for Research, Washington D.C. Antibody 1B2 can be obtained from the American type Culture Collection as ATCC Accession number 2199.

The hyperblebbing *N. gonorrhoeae* of the present invention is exemplified by a novel strain designated $WR302^{++}$, a derivative of a nonhyperblebbing strain WR302. WR302 can be obtained from Dr. Daniel Stein. $WR302^{++}$ was deposited under the provisions of the Budapest Treaty with the American Type Culture Collection, 12301 Parklawn Drive, Rockville Md. on Oct. 16, 1996, under accession no. ATCC 55857.

Blebosomes can be easily isolated from non-piliated cells. For example, blebosomes can be recovered by differential centrifugation and filtration. Alternatively, high speed centrifugation can be used. Please see Buchanan & Arko, 1977, *J. Infect. Dis.* 135:879–887 for a general reference for bleb isolation.

The blebosomes can be stored at 4° C. prior to use, or fixed if fixation does not interfere significantly with the ultimate utility of the blebosome whether as a protein production system, a diagnostic reagent, or a vaccine delivery system. Alternatively, the *N. gonorrhoeae* colonies producing blebosomes with the desired antigen can themselves be used in assays while growing on agar. Further, the bacteria can be lyophilized and stored for use after reconstitution.

Methods for Producing Protein using Blebosomes

In one embodiment, the present invention relates to a method for the production of large amounts of protein. The gene of the desired protein can be introduced into the Neisseria using vectors capable of replicating in the gonococcus and able to be introduced to the gonococcus by transformation or conjugation.

The protein can be expressed either on the surface or inside the blebosome depending upon the presence or absence of a signal sequence functionally, cloned next to the desired protein. Suitable signal sequence for expressing the desired protein on the surface of the blebosome include the H8 lipoprotein signal sequence, the PIII export sequence or the piliA import sequence.

The blebosomes expressing the desired proteins can be collected according to methods mentioned above and either used directly or accompanied by other agents of choice. Preferably, the proteins can be collected by immunological precipitation using monoclonal antibodies specific for the protein of interest.

Suitable proteins for expression include cytokines such as interleukins 1–12, and outer membrane proteins such as OspA, P6 or PspA. Several different antigens or proteins can be simultaneously expressed in the same gonococcus, if desired.

Vectors for Genetic Manipulation of Neisseria

Examples of vectors which could be used in accordance with this invention include, but are not limited to pLES2 (Stein et al. 1983, *Gene* 25:241–247) and pLEE10 (Sandlin et al. 1993, Infect. *Immun.* 61:3360–3368).

Methods for introducing said vectors and analyzing the transformants are known and within the skill of a person with ordinary skill in the art.

Vaccine Delivery System Based on Blebosomes

In a further embodiment the present invention relates to the use of blebosomes as a vaccine delivery system in human and animal subjects, animal subjects including veterinary animals, livestock animals, and companion pets. The ideal strain of the present invention would possess certain characteristics some of which include the ability to produce a truncated LOS in order to maintain the adjuvency capability of the blebosome without having the immunodominant component (Chamberlain et al., *Infect. Immun.* 57: 2872–2877, 1989); the absence of the PIII protein which, if present in the gonococcal vaccine, has been shown to stimulate an immune response that interferes with the immunogenicity of the other antigens present in the vaccine (Young & Garbe, Res. Microbiol. 142:. 55–65, 1991); the ability to stimulate the development of both humoral and cellular immune responses, and provide both systemic and mucosal immunity; the ability to grow easily and stably express the various recombinant proteins; and finally, and most importantly, the ability to bleb freely.

The vaccines of the present invention could be used to develop a protective immune response against diseases caused by bacteria such as Clostridium tetani, Streptococcus pneumoniae and Borrelia burgdorferi. The vaccines of the present invention could be used to develop a protective immune response against diseases caused by microorganisms, viruses, fungi, and protozoa.

The N. gonorrhoeae of the present invention can be engineered to express and direct any heterologous gene of a desired antigen which would elicit an immune response in a patient.

The N. gonorrhoeae of the present invention would produce high numbers of blebs with said desired antigen. The blebosomes can then be purified away from the bacterial debris and administered with or without excipients to a patient or animal as a vaccine. Alternatively, the antigen can be purified from the blebosome further to provide an antigen for use as a vaccine.

Vaccines can also be constructed by conjugating mutant Neisseria to carriers using techniques known in the art. For example, a vaccine which employs Neisseria derived proteosomes as a chemically conjugated carrier for the Hemophilus influenzae capsular polysaccharide has already been approved by the U.S. Food & Drug Administration for human use and is currently available. In a like manner, the mutants of the present invention could be also be conjugated to bacterial polysaccharides.

Vaccines may be prepared from one or more immunogenic antigen or blebosome. The preparation of vaccines which contain an immunogenic antigen(s) as an active ingredient is known to one with ordinary skill in the art. Typically, such vaccines are prepared as injectables, either as liquid solutions or suspensions; solid forms suitable for solution in, or suspension in, liquid prior to injection may also be prepared. The active immunogenic ingredients are often mixed with excipients which are pharmaceutically acceptable and compatible with the active ingredient. Suitable excipients are, for example, water, saline, dextrose, glycerol, or the like and combinations thereof. In addition, if desired, the vaccine may contain minor amounts of auxiliary substances such as wetting agents, pH buffering agents, and/or adjuvants which enhance the effectiveness of the vaccine.

The vaccines are conventionally administered parenterally, by injection, for example, either subcutaneously or intramuscularly. Additional formulations which are suitable for other modes of administration include suppositories and, in some cases, oral formulations. In addition, the vaccine containing the blebosomes or antigen(s) purified therefrom may be administered in conjunction with other immunoregulatory agents, for example, immune globulin.

The vaccines may be administered in a manner compatible with the dosage formulation, and in such amount as will be prophylactically and/or therapeutically effective. The quantity to be administered, which is generally in the range of 5 micrograms to 250 micrograms of blebosomes or antigen purified therefrom per dose, depends on the subject to be treated, capacity of the subject's immune system to synthesize antibodies, and the degree of protection desired. Precise amount of active ingredient required to be administered may depend on the judgment of the practitioner and may be peculiar to each subject.

Assays Using Blebosomes

In another embodiment, the present invention relates to a method of detecting the presence of antibodies against a disease in a sample. Using standard methodology well known in the art, a diagnostic assay can be constructed by coating on a surface (i.e. a solid support) for example, a microtitration plate or a membrane (e.g. nitrocellulose membrane), all or part of a blebosome containing the a specific antigen of the disease to be detected, and contacting it with a sample from a person or animal suspected of having said disease. The presence of a resulting complex formed between the blebosome and antibodies specific therefor in the sample can be detected by any of the known methods common in the art, such as fluorescent antibody spectroscopy or colorimetry. This method can be used, for example, for the diagnosis of viral diseases such as rabies or hepatitis, bacterial diseases such as salmonella or pneumonia, fungal diseases and parasitic diseases.

In another embodiment, the present invention relates to a diagnostic kit which contains blebosomes with the desired antigen(s) and ancillary reagents that are well known in the art and that are suitable for use in detecting the presence of antibodies to disease, said antibodies present in samples from a suspected patient.

EXAMPLES

The following non-limiting examples illustrate the invention in more detail. The examples provided describe the use of the non-selective spot transformation technique for the production of deletion derivatives. It would not be difficult for someone with ordinary skill to the art to apply the methodology for the transformation of an N. gonorrhoeae strain into a hyperblebbing N. gonorrhoeae, using the hyperblebbing phenotype for the detection of transformants.

The following materials and methods were utilized in the examples that follow.

Strains and Plasmids

Recombinant clones utilized in this study have been described previously (Gunn et al., 1992, J. Bacteriol. 174:5654–5660) and are diagramed in FIG. 1. Strain FA 19 was obtained from Dr. W. Shafer, Emory University. For clarity, the nomenclature used for gonococcal DNA R/M systems used in this study is shown in Table 1.

Media and Buffers

All N. gonorrhoeae cultures were grown in GCP broth (Difco; Detroit, Mich.) plus Kellogg's supplements (Kellogg et al., 1963, J. Bacteriol. 85:1274–1279) and sodium bicarbonate (0.042%) or on GCK agar. E. coli cultures were grown in LB broth or on LB plates (Miller, 1982, Cold Spring Harbor Laboratory, Cold Spring Harbor, N.Y.). When needed, ampicillin (35 $\mu$g/ml), kanamycin (30 $\mu$g/ml), or chloramphenicol (35 $\mu$g/ml) were added to the growth medium. Nalidixic acid (1 $\mu$g/ml) or erythromycin (2 $\mu$g/ml) were added to N. gonorrhoeae growth medium as needed.

Chemicals, Reagents and Enzymes

Chemicals were of analytical grade or higher and were purchased from Sigma Chemical Co., (St. Louis, Mo.). Restriction endonucleases were purchased from New England Biolabs (Beverly, Mass.) or Promega (Madison, Mich.) and were used with the supplied buffers according to the manufacturer's instructions.

Genetic Transformations

E. coli transformations were accomplished via the standard $CaCl_2$ procedure (Sambrook et al., 1989, Molecular cloning: a laboratory manual, 2nd ed. Cold Spring Harbor Laboratory Press, Cold Spring Harbor, New York). M13mp18 and M13mp19 replicative forms were transformed into JM101 via the standard $CaCl_2$ procedure and plated in a 3 ml overlay containing 0.3 mM IPTG, 1 mg X-gal and 100 µl of an overnight JM101 culture. N. gonorrhoeae was transformed by one of two methods. Piliated cells were resuspended to approximately $1 \times 10^8$ cells/ml in GCP broth containing 10 mM $MgCl_2$, 1× Kellogg's and 0.042% $NaHCO_3$. The cells plus DNA (1 µg) were incubated with agitation for three hours at 37° C. before plating on appropriate media. In the second method, called the spot transformation technique, piliated cells were resuspended to moderate turbidity (Klett=35) in GCP plus 10 mM $MgCl_2$. This culture was diluted $10^{-5}$ and $10^{-6}$ (in GCP+$MgCl_2$), and 10 µl of each dilution mixed with DNA (100 ng of linearized or supercoiled form), and the DNA/cell mixture was spotted onto agar plates. After overnight incubation, individual colonies within the spot were picked and streaked for isolation several times. Single isolated colonies were then screened for the desired generic make-up.

Detection of ENase/MTase Activity

Commercially available ENases that recognize the same site as the gonococcal enzymes (isoschizomers) were used to determine if a clone carried a functional MTase gene. A clone carrying a functional MTase should be resistant to cleavage by its corresponding ENase or isoschizomer. All systems except S.NgoVII have isoschizomers that enable detection by this method. No perfect isoschizomer is known for the S.NgoVII system [5'-GC(G/C)GC-3'], but the MTase protects against R.HaeIII (5'-GGCC-3') digestion if its recognition sequence is followed by a cytosine or preceded by a guanine and has the appropriate base in the variable position. The S.NgoVII MTase also protects against digestion at approximately half of all Fnu4HI sites (5'- GCNGC-3').

Methylase activity was also detected with strain AP1-200-9 (Piekarowicz et al., 1991, Nucl. Acids Res. 19:1831–1835). This strain contains a temperature sensitive mcrB allele that, when activated by methylated DNA at the permissive temperature, causes DNA damage. DNA damage then induces a chromosomal dinD::lacZ fusion. Cells were transformed with plasmids containing a potential MTase gene and grown on LB+Amp (100 µg/ml)+X-gal (35 µg/ml) plates overnight at 42° C. Plates were then shifted to 30° C. for three hours and then re-incubated at 42° C. A colony containing a plasmid with a functional MTase gene will activate the dinD::lacZ fusion and result in a blue colony.

The presence of ENase activity was determined by one or more of the following methods: (1) Reduction in the EOP of Lambda phage (ii) Reduction in the transformation efficiency of pFT180 or (iii) Protein isolation techniques. Lambda phage harvested from DH5αMCR was used to infect DH5αMCR harboring the vector alone or a suspected ENase encoding clone. A reduction in the EOP was used as a measure of ENase activity. Plasmid pFT180 (isolated from D H5aMCR) was used to transform DH5αMCR containing a suspected ENase clone and DH5αMCR containing the vector alone. A reduction in transformation frequency of the experimental vs. the control was used as an assessment of ENase activity. ENases were purified from E. coli containing ENase genes via FPLC by the method of Piekarowicz et al., 1988, Nucl. Acids Res. 16:5957–5972.

Southern Blot Analysis

Digested chromosomal DNAs were electrophoresed on 1% TBE agarose gels, transferred onto Genescreen (DuPont, Wilmington, Del.) membranes using the alkaline transfer method of Reed and Mann (1985, Nucl. Acids Res. 13:7207–722 1), and fixed onto the membrane by UV exposure (1.5 J/sq.cm). Hybridization and visualization of blots was accomplished with the use of Lumi-Phos and the Genius kit (Boehringer Mannheim, Indianapolis, Ind.). All of the steps followed the manufacturer's protocol except for the following: membranes were washed with 1× SSC, 0.1% SDS and 0.1× SSC, 0.1% SDS at 65° C.; 1% non-fat dry milk was used as the blocking agent and in the hybridization solution; and the anti-digoxigenin antibody was diluted 1:10000 instead of 1:5000. Colony blots were performed by the method of Sambrook et al. (1989).

Construction of pUP1-1

Two primers were annealed, phosphorylated and ligated to BamHI digested pUC19. Introduction of these annealed primers into pUC19 was confirmed by DNA sequencing. The sequence of the multiple cloning site in this vector is: 5'. . . GAATTCGAGCTCGGTACCCGGGGATCAGAATT-CAGACGGCTGATCC . . . TCTAGAGTCGACCTGCAG-GCATGCAAGCTTGG . . . 3' (SEQ ID NO: 1 and SEQ ID NO: 2). In the above sequence, the primer sequence is underlined and the gonococcal uptake sequence is bolded. This primer has an EcoRI site in it; therefore, digestion with EcoRI will result in the loss of half of the multiple cloning site but not the gonococcal uptake sequence.

DNA Sequencing/DNA Sequence Analysis

Genes encoding the enzymes of the S.NgoI, II, and VII R/M systems were sequenced by the Sanger dideoxy technique using the Sequenase kit (US Biochemicals, Cleveland, Ohio). DNA was sequenced using a combination of single-strand M13 clones and double-strand plasmid clones. Double-strand templates were denatured prior to labeling by the following protocol. Denaturing solution (2 µl of N NaOH, 2 mM EDTA) was added to 1 µg of plasmid DNA in a final volume of 22 µl. After a 5 min. incubation at room temperature, 8 µl of 1 M Tris (pH 4.5) was added and the DNA was precipitated. Primers obtained from The University of Maryland Biopolymer Laboratory or Walter Reed Army Institute for Research were used in the sequencing of S.NgoI, II, VII and VIII genes. Sequencing reactions were electrophoresed on a 4% polyacrylamide, 8 M urea wedge gel in an LKB sequencing apparatus.

DNA sequences were analyzed with the use of the computer programs GENEPRO (Riverside Scientific, Seattle, Wash.) and PC/GENE (Intelligenetics).

Construction of R/M Deletion Mutations

S.NgoII

The S.NgoII clone, pLV 155, was digested with NcoI and HpaI, and the NcoI end was filled in with Klenow. This reaction mixture was diluted, ligated and the DNA was transformed into strain DH5αMCP. A transformant was identified that contained a clone lacking the 1272 bp NcoI-HpaI fragment (pLV 156). This clone lacks MTase and ENase activities as demonstrated by sensitivity to HaeIII digestion and a six log increase in the efficiency of plating of lambda phage on E. coli containing these plasmids (data not shown). Strain FA 19 was transformed with this plasmid via the spot technique, and the resulting colonies were picked and grown to isolate the naturally occurring 4.2 Kb plasmid (cryptic plasmid) found in most gonococci (cryptic plasmid). A strain was identified whose cryptic plasmid was susceptible to HaeIII digestion (called JUG025).

S.NgoV

The S.NgoV clone, pJM5, was digested completely with SspI and relegated, which deleted a 722 bp region overlapping the MTase gene and the putative ENase gene. This plasmid, pJM 10, was now sensitive to digestion with BamHI, demonstrating the loss of MTase activity (data not shown). Plasmid pJM10 was used to transform *N. gonorrhoeae* strain JUG025. Since the gonococcal cryptic plasmid does not contain any S.NgoV sites, transformants that had incorporated this deletion into the chromosome were identified by lack of hybridization to plasmid pUCV51, which contains one of the deleted SspI fragments. Several colonies were identified that did not hybridize to this plasmid. One strain was chosen for further study and is called JUG026.

S.NgoIV

The S.NgoIV clone, pCBB49.1, was digested completely with BglI and partially with SspI. The BglI end was blunted with T4 DNA polymerase and the DNA was ligated. Upon screening transformants, a clone was identified that had lost the 200 bp BglI-SspI fragment (pCBB49.17). This clone is deficient in both MTase and ENase activities (data not shown). A NotI fragment containing the entire insert of pcBB49.17 was cloned into p[Bluescript SK-. A KpnI-SacI fragment of this clone, which again contained the entire insert, was cloned into the plasmid pUP1-1 to produce plasmid pUP49.17. This step was necessary since no gonococcal uptake sequence had been identified on this clone. Strain JUG026 was transformed with this construct via the spot technique. Several colonies were picked and grown, and cryptic plasmid was isolated from these cultures. A strain, JUG027, was identified that contained cryptic plasmid susceptible to NgoMI digestion.

S.NgoVII

The S.NgoVII clone, pE63, was digested with SalI (the 5'extension filled in with Klenow). This DNA was partially digested with SspI (there is one SspI site in the vector). The DNA was ligated and a clone lacking both ENase and MTase activities was identified that had lost the 1159 bp SalI-SspI fragment (pE640) (data not shown). Plasmid pE640 was ligated to plasmid pUP1-1 and an EcoRI dimer of both plasmids was identified (pPUF7). Strain JUG027 was transformed with plasmid pPUP7, and transformants that had incorporated the deletion were identified via colony blots by lack of hybridization to plasmid pE641 (which contains the deleted SalI-SspI fragment). The resulting strain was labeled JUG028.

S.NgoI

The S.NgoI clone, pUPK30, was digested with DraI. There are three DraI sites in the insert and none in the plasmid vector (pKl8). A clone containing a partial (652 bp) DraI deletion was identified and named pUPK32. This clone lacked MTase and ENase activity, as demonstrated by sensitivity to HaeII digestion and a three log decrease in the efficiency of plating of lambda phage on *E. coli* containing these plasmids (data not shown). Strain JUG028 was transformed with pUPK32, and potential transformants were screened for the incorporation of the deletion by probing colony blots with a plasmid containing the 652 bp DraI fragment. Several colonies were identified that did not hybridize to the probe. The colony picked for further analysis was called JUG029.

Results

Analysis of R/M gene clones

Recombinant clones encoding the DNA MTases of the S.NgoI, II, IV, V, and VII systems have been previously reported (Gunn et al., 1992; Sullivan and Saunders, 1988; Stein et al., 1995). The specificities of these systems are shown in Table 1. Two of these recombinant clones, encoding the S.NgoII and S.NgoIV R/M systems, have been characterized and sequenced (Sullivan and Saunders, 1988; Stein et al., 1992). The expression of MTase genes of the S.NgoI, II, IV and V systems from recombinant plasmids was verified by demonstrating the resistance of these plasmids to digestion with an isoschizomer of the system being examined. The detection of a deletion in the NgoVII R/M system is indirect, because there are no perfect isoschizomers for this enzyme. The enzyme Fnu4HI recognizes the sequence GGNCC. This means that ½ of the Fnu4HI sites will be protected by M.NgoVII. The loss of the M.NgoVII from the gonococcus will result in more sites being cleaved by this enzyme. If chromosomal DNA from a strain that lacks M.NgoVII is digested with Fnu4HI, the resulting bands will in general be of lower molecular weight.

The location of the methylase genes on these plasmids was determined by testing the ability of various deletion subclones to induce a positive signal in a DNA methylase tester strain (Piekarowicz et al., 1991). The presence of a functional ENase gene was determined by at least one of the following procedures: demonstrating a reduction in the efficiency of plaguing of phage lambda by *E. coil* cells containing the clone; showing the ability of cells containing the clone to restrict transforming DNA; or isolating proteins with ENase activity from cells containing the plasmids. Using at least one of these assays for each system, we were able to detect both ENase and MTase activity in clones encoding NgoI, II, IV and VII and MTase but no ENase activity for the NgoV clone (data not shown). Using deletion and subclone analysis, we localized the DNA encoding these genes (see FIG. 1 for restriction maps). DNA sequence analysis showed that although the NgoV clone lacked ENase activity, it contained a partial ORF downstream of the MTase gene, and this ORF was positioned similarly to the ENase gene in the other R/M systems. We believe that this ORF represents the NgoV ENase.

Construction of Plasmid Deletions and Identification of Gonococcal Transformants Containing Chromosomal Deletions In order to construct a R/M deficient gonococcal strain with transformation techniques, the transforming DNA must contain a gonococcal uptake sequence. Because no gonococcal uptake sequence was identified in the DNA sequence of our clones that encoded the NgoIV and NgoVII R/M systems (data not shown), a plasmid vector containing a gonococcal uptake sequence was constructed (pUP1-1). This was accomplished by inserting a linker containing this sequence into the BamHI site of pUC19. Since pUC19 does not replicate in the gonococcus, when the DNA deletions of interest are cloned into this plasmid and then introduced into the gonococcus by transformation, the deletions are either lost from the cell or enter the chromosome via homologous recombination.

Because we wished to disrupt multiple genes, inactivation of the desired gene by the insertion of a selectable marker was not practical. Information from restriction mapping was used to construct deletions that overlap the linked MTase and ENase genes of the S.NgoI, II, IV, V, and VII systems. FIG. 1 shows the DNA inserts of each plasmid clone and the segments that were deleted on each insert. These deletions were specific for the predicted ENase and MTase ORFs and ranged in size from 1.8 Kb (NgoII) to 200 bp (NgoIV). All deletions were constructed in such a way that there was at least 100 bp of gonococcal DNA flanking the deletions. This is the minimum size needed for efficient recombination with homologous regions of the chromosome (DCS, unpublished observations).

Because there was no selection for successful recombination of these deletions onto the chromosome, the following technique was used to identify transformants that had acquired the desired deletion. This procedure is based on the fact that all gonococcal cells are competent to take up extracellular DNA. Because of this, if a limited number of cells is incubated with an excess amount of DNA, all cells should acquire the transforming DNA. The chance of identifying a transformant that acquired the deletion would only be limited by the efficiency of the gonococcus to incorporate the deletion into its chromosome. Piliated cells were swabbed from a plate and resuspended in GCP broth plus 10 MM $MgCl_2$ to moderate turbidity (Klett=35). The cells were vortexed and diluted in $GCP+MgCl_2$. Ten-fold dilutions of the cells were prepared, a 10 $\mu$l aliquot of each dilution was mixed with approximately 0.1–0.5 $\mu$g of DNA, and the DNA/cell mixture was spotted onto the surface of an agar plate. After overnight incubation, isolated colonies within the spot were picked and re-streaked. A single colony was re-streaked at least twice more before testing colonies for incorporation of the deletion. This is necessary for two reasons: (i) a cell may have divided before acquiring the DNA, resulting in a mixed population of cells: those that had recombined the deletion into its chromosome, and those that had not; and (ii) Piliated gonococci clump and most colonies are not derived from a single cell. Using this technique, *N. gonorrhoeae* strain FA19 was successively transformed with each deletion construct. This transformation technique worked well and at least 20% of the colonies examined in each experiment acquired the desired deletion.

Two methods were used to verify that the desired deletion had been introduced into the chromosome. Chromosomal DNA was isolated from potential transformants and incubated with the isoschizomer of the system that was being deleted. Successful digestion of this DNA indicated loss of MTase function and demonstrated that the deletion had been incorporated. To verify that the loss of function was due to a deletion and not to insertional inactivation, we probed colony blots of potential transformants with a part of the DNA fragment that had been deleted from the plasmid clone. Colonies that failed to hybridize to the probe must have incorporated the deletion. All of the colonies that were tested that no longer expressed the methylase understudy bound the methylase-specific probe.

A Southern blot was performed to compare digestions of FA19 and the JUG029 (the strain containing deletions of the NgoI, II, IV, V, and VII R/M systems). Each set was digested with the appropriate enzymes, electrophoresed, and blotted. The membrane was cut into strips and each strip was probed with DNA that traverses the deleted region in each of the five R/M systems. Set 1 was digested with DraI and probed with the PstI-XhoI fragment of pUPC30. Chromosomal DNA from JUG029 was missing the 652 bp DraI fragment. In set 2, the NgoII system was examined. JUG029 was missing the 1414 bp Sau3AI band that spans the deletion. The second hybridizing band was larger than the FA19 band. Subsequent analysis of Southern blots of chromosomal DNA digested with other enzymes demonstrate that the deletion extends further upstream of the NcoI site (data not shown). The NgoIV system was examined in set 3. SspI digested chromosomal DNA showed the expected loss of the 400 bp SspI fragment and the subsequent 250 bp increase in size of the largest SspI fragment. In set 4, chromosomal DNA was digested with RsaI to confirm the NgoV deletion. The deletion strain lacks the 452 bp and 684 bp fragments due to the loss of the RsaI sites at positions 1075 and 1527. The expected increase in size of the largest fragment can also be observed. Set 5 examined the NgoVII deletion. Chromosomal DNA was digested with EcoRI+HindIII. The hybridizing EcoRI-HindIII fragment is 1.2 Kb less than that of FA19.

To demonstrate loss of biological MTase activity of the five R/M systems that were deleted in JUG029, chromosomal DNA was isolated and incubated with the isoschizomers of the systems that were deleted. Successful digestion of the chromosomal DNA would indicate the functional loss of the MTase. While FA19 chromosomal DNA remains undigested with isoschizomers of NgoI, II, IV and VJUG029 digestion appears to go to completion. In analyzing the NgoVII system, it is apparent that chromosomal DNA isolated from JUG029 is digested to a greater extent than chromosomal DNA isolated from FA19. Taken together, these data demonstrate that the appropriate deletions were all successfully introduced into the chromosome, and that JUG029 possessed the appropriate methylation defective phenotype.

Comparison of the Transformation Frequency of FA19 vs. JUG029

To determine if the loss of five ENases would make the gonococcus more amenable to transformation with DNA propagated in *E. coli*, JUG029 and FA19 were transformed with pSY6 and pRDL2. Plasmid pSY6 contains DNA that encodes a mutant DNA gyrase (Stein et al., 1991). When this mutation is introduced into the chromosome, cells become resistant to nalidixic acid. Transformation with this plasmid should not be affected by the endogenous ENases because nalidixic acid resistant transformants arise as a recombination between the linearized plasmid DNA and the host chromosome. The data presented in Table 2 show that the transformation frequency to NalR with pSY6 was similar for both strains ($1.8 \times 10^{-4}$ for FA19 vs. $1.7 \times 10^{-4}$ for JUG029).

TABLE 2

Examination of in vivo restriction by FA19 and JUG029

| Strain | pSY6 (DH5αMCR)[b] | pRDL2 (F62)[c] | pRDL2 (DH5αMCR) |
|---|---|---|---|
| FA19 | $1.8 \times 10^{-4}$ | $2.2 \times 10^{-6}$ | $<1.6 \times 10^{-9}$ |
| JUG029 | $1.7 \times 10^{-4}$ | $4.1 \times 10^{-6}$ | $1.5 \times 10^{-8}$ |

[a]*N. gonorrhoeae* strains were transformed with 35 ng of pSY6 or 0.5 $\mu$g of pRDL2 and incubated for 3 hours at 37° C. with shaking before being plated on appropriate media. Transformation frequency is the number of transformants per CFU per ml. The frequencies presented are from a single experiment; however, the experiment was repeated three times with no significant differences between trials.
[b]pSY6 contains a mutant form of the DNA gyrase gene that, upon recombination with the host chromosome, provides the cell with resistance to nalidixic acid.
[c]pRDL2 is a pLEE20 derivative (Ery[R]) which contains a 456 bp gonococcal DNA insert containing an uptake sequence. When this plasmid is isolated from a fully MTase proficient gonococcal strain (F62 in this case), it is methylated and upon transformation, should not be subject to host restriction.

In order for a plasmid to successfully transform the gonococcus, it must recircularize and form a functional plasmid. Plasmid pRDL2, a pLEE20 derivative carrying a 456 bp gonococcal DNA fragment containing one copy of the uptake sequence, can be grown in *E. coli* or *N. gonorrhoeae*. Therefore both methylated (from *N. gonorrhoeae*) and non-methylated (from *E. coli*) pRDL2 can be used in the transformation assays. Methylated pRDL2 should not be restricted upon transformation of the gonococcus, but non-methylated pRDL2 may be subject to host restriction. The plasmid transformation frequencies using methylated pRDL2 were similar for FA19 and JUG029 ($2.2 \times 10^{-6}$ and $4.1 \times 10^{-6}$, respectively). Transformation with non-methylated pRDL2 resulted in a few transformants in JUG029 ($1.5\times10^{-8}$) but none in FA19 ($<1.6\times10^{-9}$). This data demonstrates that although JUG029 is still able to restrict transforming DNA, a measurable reduction in its restriction ability can be detected. This indicates that at least some of the remaining ENases are able to participate in host mediated restriction.

References

Biswas et al, (1977) *J. Bacteriol.* 129:983–992.

Biswas and Sparling, (1981) *J. Bacteriol.* 145:638–640.

Butler and Gotschlich, (1991) *J. Bacteriol.* 173:5793–5799.

Drazek et al, (1995) *J. Bacteriol.* (177(9):2321–7).

Goodman and Scocca, (1988) *Proc. Natl. Acad. Sci.* 85:6982–6986.

Gunn et al, (1992) *J. Bacteriol.* 174:5654–5660.

Kellogg et al, (1963) *J. Bacteriol.* 85:1274–1279.

Korch et al, (1983) *J. Bacteriol.* 155:1324–1332.

Mathis and Scocca, (1984) *J. Gen. Microbiol.* 130:3165–3173.

Miller, (1982) Experiments in molecular genetics. Cold Spring Harbor Laboratory, Cold Spring Harbor, N.Y.

Piekarowicz et al, (1988) *Nucl. Acids Res.* 16:5957–5972.

Piekarowicz et al, (1991) *Nucl. Acids Res.* 19:1831–1835.

Reed and Mann, (1985) *Nucl. Acids Res.* 13:7207–7221.

Sambrook et al, (1989) Molecular cloning: a laboratory manual, 2nd ed. Cold Spring Harbor Laboratory Press, Cold Spring Harbor, New York.

Sandlin and Stein, (1994) *J. Bacteriol.* 176:2930–2937.

Sox et al, (1979) *J. Bacteriol.* 138:510–518.

Sparling (1966) *J. Bacteriol.* 124:1364–1371.

Stein et al, (1988) Role of restriction and modification on genetic exchange in *Neisseria gonorrhoeae*. In Gonococci and Meningococci. Poolman et al (eds). 5th International Neisseria Conference. Kluwer Academic Publishers, Dordrecht, Netherlands. pp. 323–327.

Stein et al, (1991) *Antimicrob. Agents Chemother.* 35:622–626.

Stein (1991) *Can. J. Microbiol.* 37:345–349.

Stein et al, (1992) *J. Bacteriol.* 174:4899–4906.

Sullivan and Saunders, (1988) Determination of the endonuclease and methylase content of *Neisseria gonorrhoeae* strain P9 and the cloning therefrom of two functional methylase genes. In Gonococci and Meningococci. Poolman et al (eds). 5th International Neisseria Conference. Kluwer Academic Publishers, Dordrecht, Netherlands. pp. 329–334.

EXAMPLE 2

Materials and Methods

Bacterial Strains. *N. gonorrhoeae* F62 was obtained from P. Frederick Sparling (University of North Carolina, Chapel Hill, N.C.). *E. coli* DH5 MCR was obtained from Bethesda Research Laboratories (Bethesda, Md.). Gonococci were grown in GCP broth supplemented with Kellogg's solution (White, L. A., D. S. Kellogg, Jr., 1965, Appl. Micro. 13:171–74) and 0.042% sodium bicarbonate and on GCK agar containing erythromycin (2 $\mu$g/ml), vancomycin (3 $\mu$g/ml), colistin (7.5 $\mu$g/ml), and nystatin (1.25 units/ml) as needed. *E. coli* DH5 MCR was grown in L broth or LB agar containing ampicillin (30 $\mu$g/ml), kanamycin (30 $\mu$g/ml), erythromycin (300 $\mu$g/ml), and x-gal (35 $\mu$g/ml) as needed.

Chemicals, reagents, and enzymes. Restriction enzymes and T4 DNA ligase were purchased from New England Biolabs (Beverly, Mass.). Chemicals used for transformation studies were reagent grade or better and were purchased from Sigma Chemical Co. (St. Louis, Mo.) unless otherwise specified.

DNA Manipulations. Plasmid DNA was isolated by the alkaline lysis procedure and purified on cesium chloride-ethidium bromide gradients (Birnboim & Doly, 1979, Nucl. Acids. Res. 7: 1513–1523). Plasmid DNA was introduced into *E. coli* using the CaCl2 transformation method (Sambrook, et al., 1989, In Molecular Cloning, 2nd ed. Cold Spring Harbor Press, Cold Spring Harbor, N.Y.).

DNA Sequencing. DNA sequencing reactions were performed by the Sanger dideoxy method (Sanger et al., 1977, Proc. Natl. Acad. Sci. (USA) 74: 5463–5467) using the Sequenase Version II sequencing kit (United States Biochemicals, Cleveland, Ohio) and -[35S] DATP (New England Nuclear, DuPont, Boston, Mass.). PCR sequencing was performed directly on the PCR products as directed using the CircumVent thermal cycle dideoxy DNA sequencing kit (New England Biolabs, Beverly, Mass.). Sequencing products were separated on a 55 cm by 0.2 mm 4% acrylamide gel (7 M urea in 1× TBE buffer (100 mM Tris, 0.083 M Boric acid, 1 mM EDTA)) with a 0.6 mm wedge (maximum thickness) in the last 10 cm. The gels were fixed, dried, and exposed to XOMAT x-ray film (Kodak) for 36 hours.

Polymerase Chain Reaction. PCR was performed using the GeneAmp PCR kit from Perkin Elmer Cetus (Norwalk, Conn.) under the recommended conditions. The 100 l reaction was performed with a one minute denaturation at 94° C. followed by a one minute annealing at 50° C. and a one minute extension at 72° C. for a total of 30 cycles. Primers used in this study for both PCR and sequence analysis were made at MedImmune. The sequence of the primers used to amplify H.8RS1 were: H.8-5', CCCTGAATTCAAATCAT-ACTGAATTAT (SEQ ID NO:3); H.8-3', CCGATCAGT-TCAAAACTGC (SEQ ID NO:4). The sequence of the primers used to add the SphI sites into H.8 were GGCTG-CATGCGGCGGAG and CCGCCGCATGCAGCCAAAG (SEQ ID NOS:5 and 6). The sequence of the primers used to amplify ospA were: OspA-5', ATTCCAGTCGACAAG-CAAAATGTTAGCAGC (SEQ ID NO:7); OspA-3', ATTC-CAGCATGCTTATTTTAAAGCGTTTTTAATTTC (SEQ ID NO:8).

Conjugation. Plasmids were introduced into gonococcal strain F62 by conjugation with *E. coli* S17-1 (Nassif, X., D. Puaoi, and M. So. 1991. Transposition of TN1545-3 in the pathogenic Neisseriae: a genetic tool for mutagenesis. J. Bact. 173:2147–2154). Conjugations were performed by filter mating and allowed to proceed for three hours. To select for gonococcal transconjugants, the cells on the filter were resuspended in GCP broth and plated on GCK containing erythromycin, vancomycin, nystatin, and colistin.

Blebosome Isolation

Western blotting. Blebosome lysates (approximately ug of total protein) were analyzed by SDS-PAGE and Western blot with the OspA-specific mAb H5332 (Green, B. A., T. Quinn-Dey, and G. W. Zlotnick. 1987. Biologic activities of antibody to a peptidoglycan-asociated lipoprotein of *Haemophilus influenzae* against multiple clinical isolates of H. influenzae type b. *Infect. Immun.* 55:2878.). Expression of OspA was compared to purified OspA lipoprotein, kindly provided by Dr. L. Erdile (Connaught Laboratories, Inc., Swiftwater, Pa.). Protein bands reacting with H5332 were visualized after incubation with a secondary antibody (goat anti-mouse IgG conjugated to horseradish peroxidase) using the nehanced chemiluminescent detection (ECL) system (Amersham Corp., Arlington Heights, Ill.) according to the manufacturer's instructions.

Triton X-114 fractionation. Blebsomes were suspended in PBS, disrupted by sonication and solubilized at 4° C. by the addition of Triton X-114 (TX114) to 2% (volume/volume) Insoluble material (cell wall-enriched fraction) was sedimented by centrifugation at 100,000×g and the supernatant was subjected to detergent phase partitioning (Bordier, C. 1981. Phase separation of integral membrane proteins in Triton X-114 solution, J. Biol. Chem. 265:1604.) After briefly warming (37° C.) the TX114 solution, separation of aqueous and detergent phases was achieved by a short centrifugation. The two phases were back-extracted three times and proteins in representative samples were precipitated by the addition of nine volumes of acetone. A portion of each culture supernatant was subjected to SDS-PAGE, transferred to nitrocellulose, and blotted with anti-OspA mAb H5332.

Immunogenicity of blebosome constructs. Sera were collected from the tail vein of immunized mice at various times after immunization and pooled for each group of mice to monitor antibody responses by ELISA. ELISA plate (Immunolon 4) were coated with 50 ul of whole Borrelia (strain 31) suspended in carbonate buffer (pH 9.6) at 10 $\mu$g/ml or with temperature or overnight at 4° C. The antigen solution was then removed and plates were incubated with blocking solution (0.5% BSA and 0.5% nonfat dry milk) in PBS with 0.1% Tween-20 (PBS-T20) for 1 h at room temperature. Two-fold serial dilutions of serum starting at 1/200 were made in blocking solution and 50ul of each dilution was added to duplicate wells of the antigen-coated plate. After an incubation at room temperature for 1 h., the plates were washed with PBS-T20 and incubated with 50ul of a 1:1000 PBS-T20 dilution of peroxidase-conjugated goat anti-mouse IgG (Kirkegaard and Perry Laboratories, Inc., Gaithersburg, Md.) secondary antibody for 1h. Color was developed with 2,2'-azino-dif[3-ethyl-benzthiazoline sulfonate] substrate reagent (Kirkegaard and Perry Laboratories, Inc.), and measured by absorbance at 405 nm on an ELISA reader (dynatech). Endpoint titers were defined as the highest dilution at which the A405 values were twice the values for normal mouse sera diluted to an equivalent concentration.

Challenge studies. Challenge doses were derived by expansion of a single colony of the low-passage B. burgdorferi sh.2 strain (Schwan, T. G., W. Burgdorfer, M. E. Crumpf, and R. H. Karstens. 1988. The urinary bladder, a consistent source of Borrelia burgdorferi in experimentally infected white-footed mice (Peromyscus leucopus). J. Clin. Microbiol. Immunized mice and control mice were challenged intradermally at the base of the tail with $10^4$ spirochetes. This represented approximately 100 $ID_{50}$ units of the B. burgdorferi Sh. 2 strain. Mice were killed 13 days after challenge, and bladder and tibiotarsal joint tissues were harvested and cultured in BSK-II media as described previously (Erdile, L. F., M. Brandt, D. J. Warakomski, G. J. Westrack, A. Sadziene, A. G. Barbour, and J. P. Mays. 1993. Role of attached lipid in immunogenicity of Borrelia burgdorferi OspA. Infect. Immu. 61:81). Cultures were monitored for 14 days by phase contrast microscopy for the presence of spirochetes. The presence of one or more spirochetes per 20 high-power fields in any culture was scored as a positive infection.

Results

Construction of Neisseria gonorrhoeae expressing OspA. N. gonorrhoeae produces a lipoprotein, H.8 as one of its normal outer membrane proteins. In order to determine if it was possible to overexpress this protein in the outer membrane of the gonococcus, the gene encoding this protein was cloned onto a high copy number plasmid, pLEE20. The DNA sequence encoding this protein was amplified via the PCR from *N. gonorrhoeae* strain F62, based on sequence information published for strain R10 (Baehret al., 1989, Mol. Microbiol. 3:49–55). Primers were designed in such a way that DNA sequences 5' of the coding sequence contained an EcoRI site, and DNA sequences 3' of the gene contained a HinDIII site. The amplified DNA was digested and inserted into pLEE20 that had been digested with EcoRI and partially digested with HinDIII. The ligated DNA was introduced into *Escherichia coli* DH5 MCR, and erythromycin resistant transformants containing the amplicon were identified. The DNA sequence was determined from one of these clones to verify that the amplified DNA encoded H.8. The data indicated that the cloned gene was H.8 (data not shown).

The H.8 encoding construct was introduced into *E. coli* strain S17-2 by transformation. This strain was used to mobilize the pLEE20-H.8 into *N. gonorrhoeae* F62 via conjugation. Transconjugants were selected on Thayer Martin media supplemented with erythromycin. SDS-PAGE profiles of F62(pLEE20-H.8) indicated that this strain expressed more H.8 than seen in wild-type strains. These experiments demonstrate that it is possible to overexpress lipoproteins in the gonococcus.

To ensure that *N. gonorrhoeae* would be able to process the Borrelia OspA signal sequence correctly, the protein was expressed as a fusion protein. In order make this fusion, an SphI site was introduced into the H.8 sequence at a site that corresponded to the cysteine that serves as a lipidation signal. The DNA sequence encoding OspA was amplified from pTRH44 (Bergstromet al., 1989, Mol. Microbiol. 3:479–486) by PCR. Primers were designed in such a way as to introduce an SphI site at a location that corresponded to the cysteine that is lipidated in OspA. The primer that corresponded to the 3' end of the gene also contained an SphI site. The amplicon and the cloning vector were digested with SphI, ligated and introduced into *E. coli* DH5 MCR. Plasmids containing the insert were identified, and the DNA sequence of the construct verified by DNA sequence analysis. This plasmid was introduced into *E. coli* S17-2, and then introduced into the gonococcus via conjugation, as described above.

Ouantitation and localization. The amount of OspA expresed in blebosomes was quantified using a quantitative Western assay in which the levels of binding of an anti-OspA mAb to blebosomes was compared to binding to purified OspA. The result of that analysis suggests that OspA represents approximately 0.2% of total blebosome protein.

To determine if expression of the OspA gene from the lipoprotein expression vector resulted in lipid acylation of recombinant OspA, blebosomes were subjected to Triton X-114 detergent phase partitioning analysis to enrich for membrane-associated lipoproteins (Bordier, 1981, J. Biol. Chem. 256:1604; Radolf et al., 1988, Infect. Immun. 56:490.). Expression of the OspA protein in association with the H8 lipidation signal sequence resulted in a product that was exclusively located in the detergent-soluble fraction, which is highly enriched for lipophilic proteins. This finding indicates that fusion of the H8 signal sequence to OspA resulted in a product that was efficiently exported and post-translationally modified in the blebosome membrane.

Immunization studies. A panel of 5 different mouse strains was analyzed for anti-OspA antibody responses following immunization with OspA-expressing blebosomes (figure sdlfdjasllkfj). The results suggest that both the endotoxin-resistance locus and other loci may control immune responses to ospA-expressing blebosomes. Thus, the C3H/HejLPS hyporesponsive strain generated substantial anti-OspA responses following boosting with OspA blebosomes whereas the related C3HeB/Fej LPS responsive strain did not, suggesting involvement of the endotoxin resistance locus in responses to blebosomes. In addition, several strains generated different responses to blebosome-expressed OspA even though they all carried the Lps allele, suggesting involvement of non-Lps-associated loci in this phenomenon. Thus, BALB/c mice generated substantial OspA responses following boosting with OspA-blebs whereas SJL/J and C57BL/6 did not.

Challenge studies. The ability of OspA-expressing blebosomes to induce protective immune responses was examined by immunizing animals and assessing their antibody responses against OspA and Borrelia whole cell lysate two weeks following two boosts. The results showed that all animals immunized with OspA blebs generated detectable anti-OspA responses, with 4/5 animals demonstrating titers greater than 1/3200. These same four animals also exhibited reactivity against a lysate prepared from whole Borrelia (the fifth animal exhibited no detectable anti-Borrelia response). None of the animals immunized with non-recombinant blebosomes generated detectable anti-OspA or anti-Borrelia responses.

These animals were challenged with live Borrelia. Two weeks after challenge, all of the animals immunized with nonrecombinant blebosomes contained recoverable Borrelia in their bladders and tibiotarsal joints. In contrast, recoverable Borrelia were only obtained from 1/5 animals immunized with OspA blebosomes. In this group, culturable Borrelia were only obtained from the animal with the lowest anti-OspA titers.

Approximately 40% of the immunized mice achieved antibody titers greater than 1:400. 100% of the mice with this antibody titer were protected from the challenge.

Discussion

The data in this example demonstrate the potential use of recombinant gonococcal blebosomes as a vaccine delivery system. Blebosomes express many of the desirable features of both living and nonliving delivery systems: while they avoid many of the disadvantages associated with the use of live delivery systems in young or immunocompromised individuals, they can be engineered to express antigens in the context of a biologic membrane that is easily purified without the use of extensive, potentially denaturing purification procedures.

In the experiments presented here, a fusion protein consisting of the OspA antigen of Borrelia burgdorferi linked to the lipidation signal sequence of the Neisseria H8 surface antigen was expressed. The intent of constructing this fusion protein using an endogenous lipidation signal was to avoid any potential problems in the transfer and/or processing of foreign signals within Neisseria. However, the lipidated surface protein P6 from Hemophilus influenzae has also been successfully expressed under control of its own lipidation signal sequence, demonstrating the localization of this antigen to the blebosome surface in a detergent-soluble form, suggesting that Neisseria is capable of recognizing and processing foreign bacterial lipidation signals.

It is apparent that multiple genetic loci may be involved in determining responsiveness to antigens presented by gonococcal blebosomes. In a limited strain survey, both the Lps locus and other unmapped loci appear to control responsiveness to OspA. Because of the known adjuvant properties associated with LPS, it is perhaps not surprising to see an effect of the Lps locus on immune responses elicited by this construct.

In the experiments described here, OspA was used as a test immunogen since responses to this antigen have been shown to be protective against challenge with OspA-expressing Borrelia isolates 0. However, not all *B. burgdorferi* isolates express this antigen 0, and some tick-borne isolates that initially express OspA have recently been shown to turn off expression following a blood meal 0. Other Borrelia antigens, in combination with OspA, may induce more broadly efficacious immune responses than OspA alone.

The results of these immunogenicity studies indicate that IgG responses can be induced against a foreign lipoprotein expressed on the surface of blebosomes. The ability of these preparations to induce OspA-specific Th or CTL was not examined. High levels of IFN-g and IL-2, but not IL-4, have been observed in culture supernatants of Neisserial lysate-stimulated lymph node cells from blebosome-immunized mice, suggesting that blebosomes may stimulate strong Th1 responses. The possibility that these preparations stimulate CTL responses awaits the cloning of antigens encoding known CTL epitopes into Neisseria. It is likely that blebosome-expressed antigens will be processed mainly through an endocytic pathway and therefore presented mainly in the context of MHC class II molecules.

The blebosomes used in these studies generated protective antibody responses without apparent toxicity. However, doses 3–5 fold higher than those reported here resulted in significant toxicity. Fur ruffling was associated with doses above 30 mg/animal and certain blebosome preparations were lethal at doses of 100 mg/animal or higher, when given intraperitoneally, particularly after boosting. These toxic effects were not diminished by giving the antigen intranasally, or when given intraperitoneally on alum. Future experiments will examine the effects of other routes of administration on toxicity, as well as the influence that modulating levels of LOS on the surface of the blebosome has on toxicity of blebosome preparations. In this regard, a series of Neisserial mutants has recently been generated that express varying levels of LOS on their surface. It will be interesting to determine whether strains expressing decreased amounts of surface LOS will maintain immunogenicity while decreasing toxicity.

In summary, gonococcal blebosomes expressing a foreign bacterial surface protein, OspA from *Borrelia burgdorferi*, are capable of inducing immune responses that protect mice against Borrelia challenge.

EXAMPLE 3

Cloning of the P6 gene of *Haemophilus influenzae*

Figure 6A:
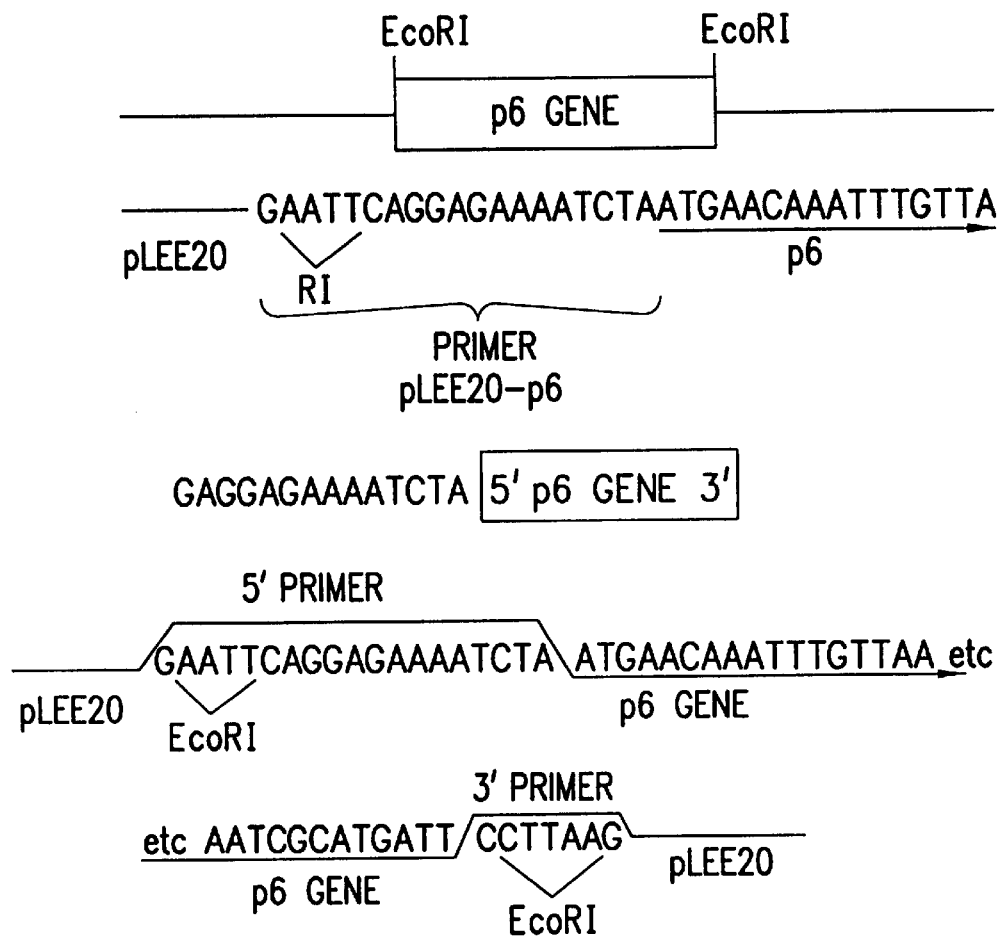
Figure 7A:
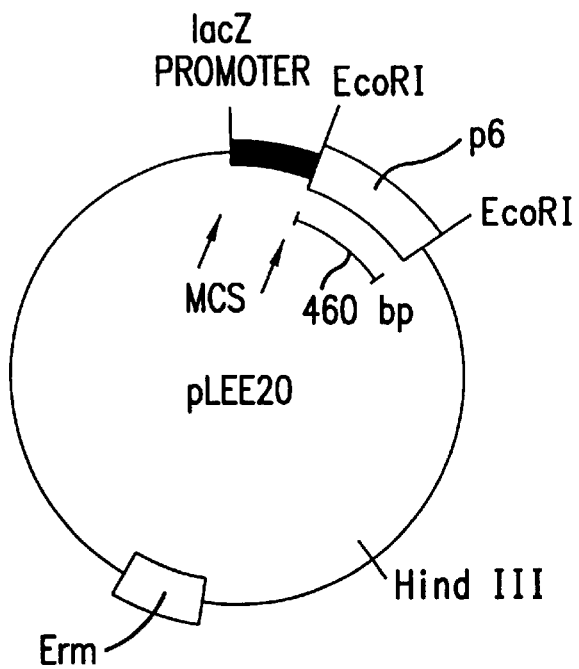
Figure 8:
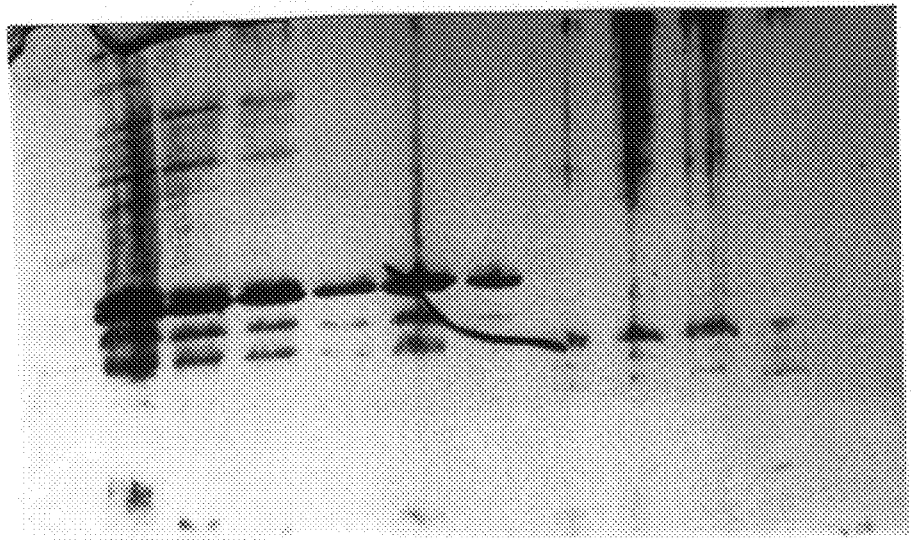
FIG. 8 is a Coomassie Blue stained SDS-PAGE gel. A#8, #18 and #19 are pLEE20-p6 clones.
Figure 9:
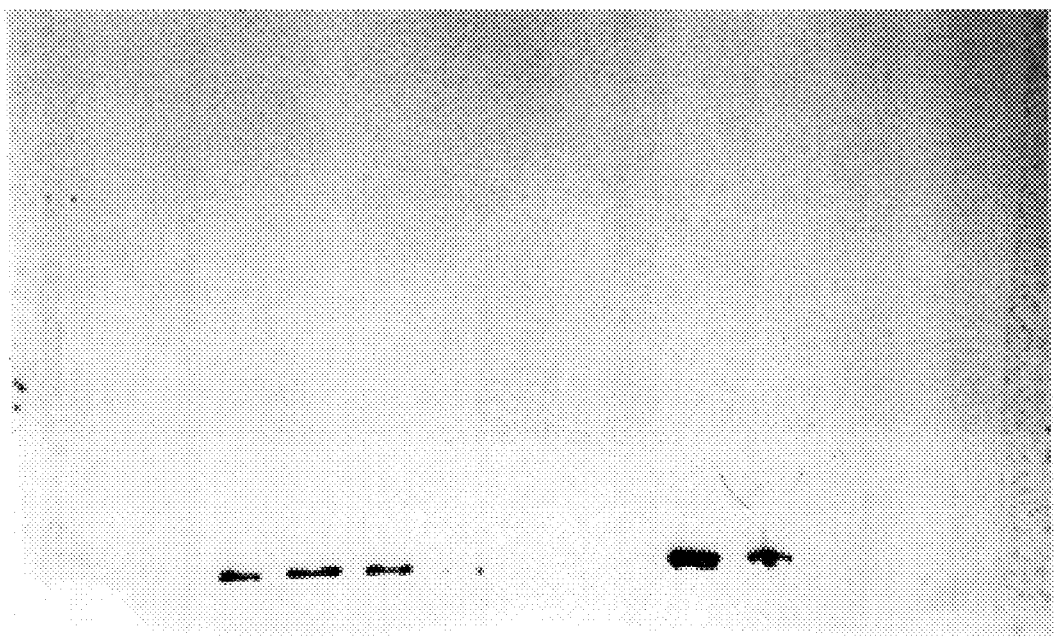
FIG. 9 is a Western blot of the SDS-PAGE gel of FIG. 8.

The P6 gene of *H. influenza* was cloned using PCR. Briefly, two primers, each flanked by EcoRI sites, were used to amplify a fragment of approximately 500 bp (FIG. 6A). The amplified fragment was cloned into pLEE20 (FIG. 7A). Clones were analyzed by restriction analysis. Clones containing the insert in both orientations were obtained. Expression was analyzed by reacting colonies with polyclonal antibodies directed to P6 protein.

pLEE20-p6 was introduced into *E. coli* strain SB17-2. Plasmids obtained from *E. coli* were introduced into *N. gonorrhoeae* F62 via conjugation. Transconjugants were screened for reactivity with antibody, and expression was verified using SDS-PAGE (FIG. 8) and Western blot (FIG. 9).

EXAMPLE 4

Cloning of the pspA gene of *Streptococcus pneumoniae*

Figure 6B:
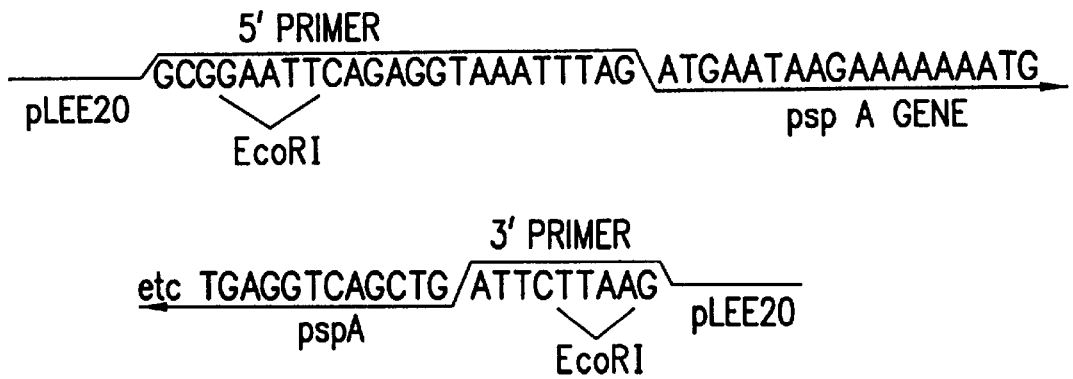
Figure 7B:
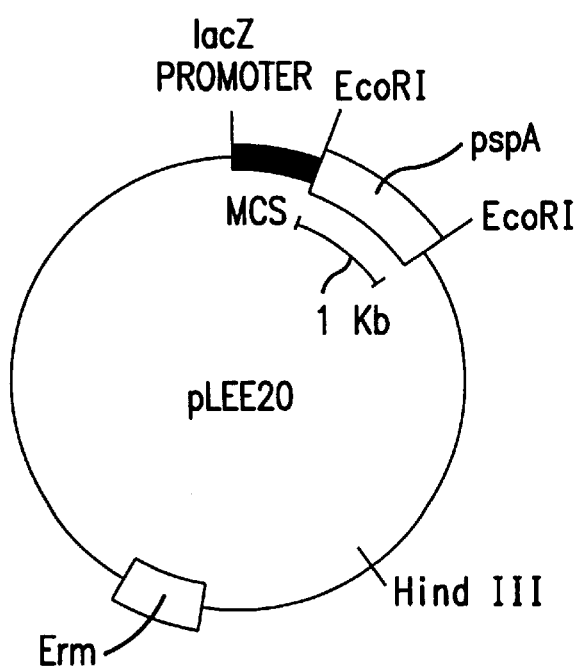

The pspA gene of S. pneumoniae was cloned using PCR. Briefly, two primers, each flanked by EcoRI sites, were used to amplify a fragment of approximately 1 kb (FIG. 6B). The amplified fragment was sequenced and cloned into pLEE20 (FIG. 7B). Clones were analyzed by restriction analysis.

pLEE20-pspA is introduced into E. coli strain SB17-2. Plasmids obtained from *E. coli* are introduced into *N. gonorrhoeae* F62 via conjugation. Transconjugants are screened for reactivity with antibody, and expression is verified using SDS-PAGE and Western blot.

This application is a continuation of U.S. Ser. No. 08/443,514 now abandoned, entitled "VACCINE DELIVERY SYSTEM", filed May 18, 1995 and the file wrapper continuation application thereof U.S. Ser. No. 08/936,552 (Attorney Docket No. 2747-095-27 FWC) now abandoned. The full text of that application is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A vaccine for providing in a subject immunity against a disease, said vaccine comprising blebosomes wherein a heterologous immunogenic polypeptide specific for said disease is expressed on the surface of said blebosomes, and wherein said heterologous immunooenic polypeptide is present in a pharmacologically effective dose in a pharmaceutically acceptable excipient.

2. The vaccine of claim 1, wherein the subject is human.

3. The vaccine of claim 1, wherein the subject is animal.

4. The vaccine of claim 1, wherein said disease is caused by a microorganism.

5. The vaccine of claim 1, wherein said disease is caused by a microorganism.

6. The vaccine of claim 3, wherein said disease is caused by a microorganism.

7. The vaccine of claim 1, wherein said disease is caused by a bacterium.

8. The vaccine of claim 1, wherein said disease is caused by a virus.

9. The vaccine of claim 1, wherein said disease is caused by a fungus.

10. The vaccine of claim 1, wherein said disease is caused by a protozoan.

11. A pharmaceutical composition for treating a disease, comprising a blebosome wherein a heterologous polypeptide active against said disease is present in a pharmacologically effective dose in a pharmaceutically acceptable excipient; and
wherein said heterologous polpeptide active against said disease is expressed on the surface of said blebosome.

12. The pharmaceutical composition of claim 11, wherein said polypeptide is a cytokine.

13. The pharmaceutical composition of claim 11, wherein said polypeptide is a receptor.

14. The pharmaceutical composition of claim 11, wherein said polypeptide is an antibiotic.

15. The vaccine of claim 1, wherein said blebosomes express OspA from *Borrelia burgodorferi*.

16. The composition according to claim 11, wherein said blebosomes express OspA from *Borrelia burgodorferi*.

17. A vaccine delivery system for eliciting a protective immune response in subject against a disease, said vaccine delivery system comprising blebosomes that express a heterologous antigen on the surface of said blebosomes.

18. The vaccine delivery system according to claim 17, wherein said disease is a disease caused by a microorganism, a bacterium, a virus, a fungus, or a protozoan.

19. The vaccine of claim 1, wherein said blebosomes are produced by *Neisseria gonorrhoeae*.

* * * * *